(12) United States Patent
Matsui

(10) Patent No.: US 7,764,367 B2
(45) Date of Patent: Jul. 27, 2010

(54) SURFACE INSPECTION METHOD AND SURFACE INSPECTION APPARATUS

(75) Inventor: Shigeru Matsui, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 336 days.

(21) Appl. No.: 11/834,217

(22) Filed: Aug. 6, 2007

(65) Prior Publication Data
US 2008/0174764 A1    Jul. 24, 2008

(30) Foreign Application Priority Data
Sep. 1, 2006    (JP)    ............... 2006-237970

(51) Int. Cl.
*G01N 21/00* (2006.01)

(52) U.S. Cl. ................. 356/237.2; 356/237.3

(58) Field of Classification Search .... 356/237.1–237.5
See application file for complete search history.

(56) References Cited

U.S. PATENT DOCUMENTS

| 5,798,829 | A | 8/1998 | Vaez-Iravani |
| 5,825,482 | A * | 10/1998 | Nikoonahad et al. ..... 356/237.2 |
| 6,760,100 | B2 * | 7/2004 | Ivakhnenko et al. ..... 356/237.2 |
| 7,002,677 | B2 | 2/2006 | Bevis et al. |

* cited by examiner

*Primary Examiner*—Michael P Stafira
(74) *Attorney, Agent, or Firm*—Crowell & Moring LLP

(57) ABSTRACT

A surface inspection method and a surface inspection apparatus in which a plurality of photodetectors are arranged in a plurality of directions so that light scattered, diffracted or reflected on a surface of an object to be inspected or in the vicinity of the surface is detected and a plurality of signals obtained by this are subjected to weighted addition processing or weighted averaging processing by linear combination.

18 Claims, 9 Drawing Sheets

FIG. 2A
PLAN VIEW
FIG. 2C
DETAIL VIEW OF AREA AROUND ILLUMINATION SPOT
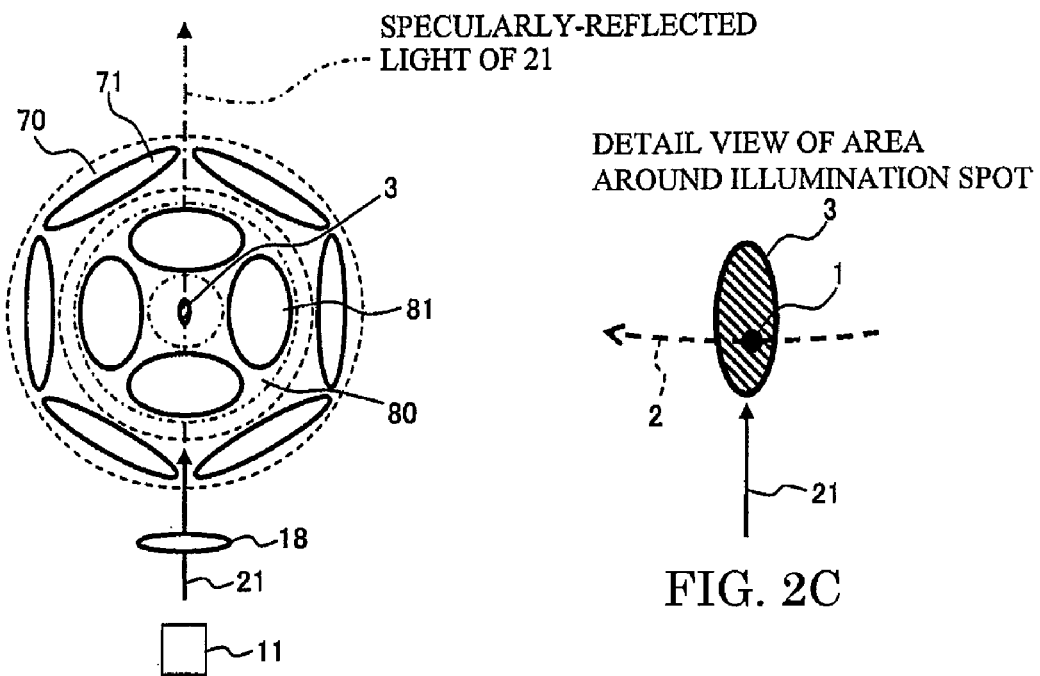
FIG. 2B
SIDE VIEW
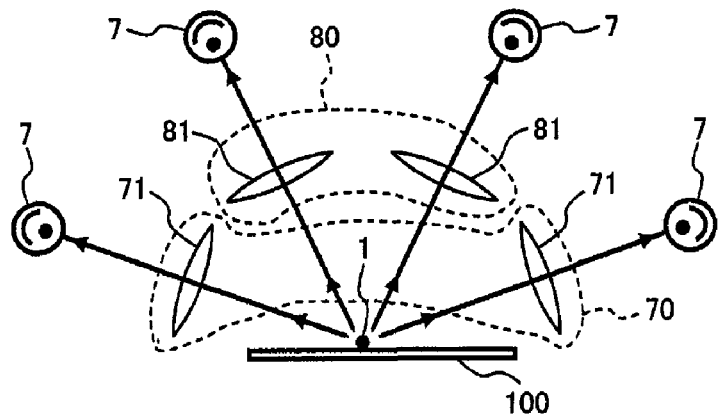

FIG. 4 A
SCATTERED LIGHT FROM CONTAMINANT PARTICLE AND DEFECT
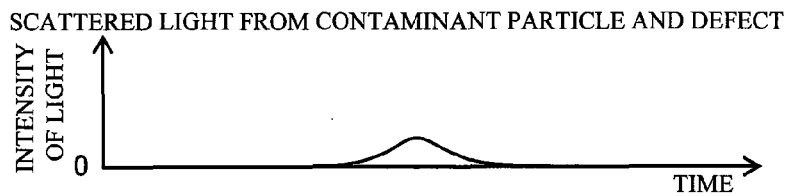

FIG. 4 B
BACKGROUND SCATTERED LIGHT
(SCATTERED LIGHT DUE TO SURFACE ROUGHNESS WITHIN ILLUMINATION SPOT)
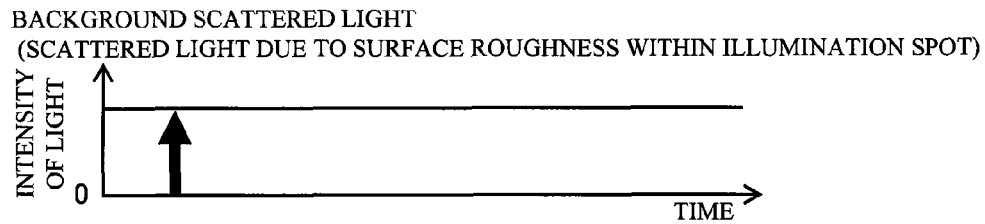

FIG. 4 C
INCIDENT LIGHT OF PHOTODETECTOR
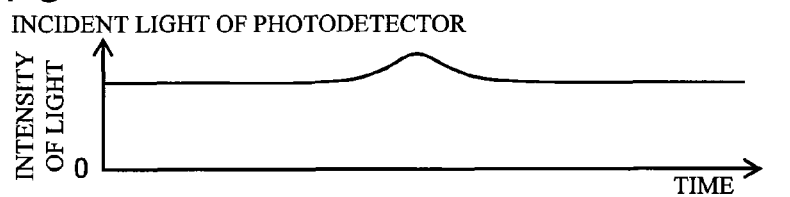

FIG. 4 D
OUTPUT SIGNAL OF PHOTODETECTOR
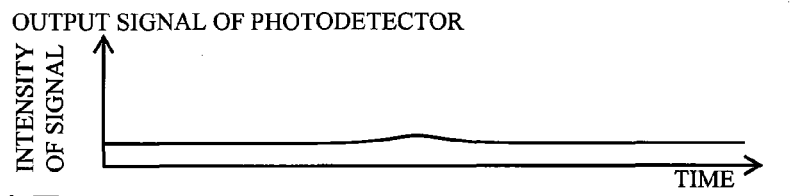

FIG. 4 E
RESULTS OF DC AMPLIFICATION OF FIG. 4D
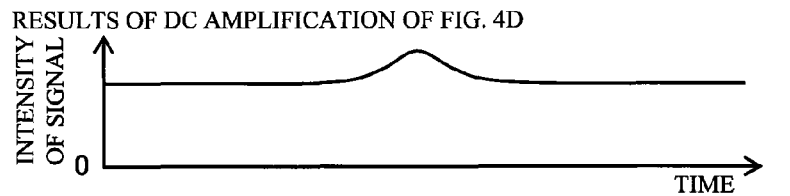

FIG. 4 F
RESULTS OF PASSING RESULTS OF FIG. 4E THROUGH BAND-PASS FILTER
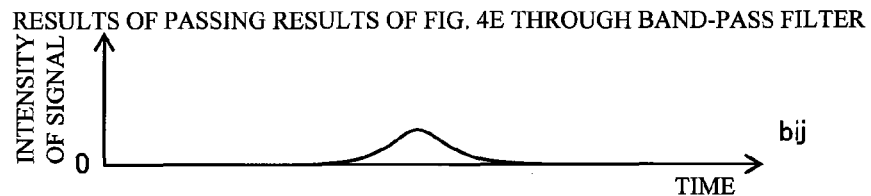

FIG. 4 G
RESULTS OF PASSING RESULTS OF FIG. 4E THROUGH LOW-PASS FILTER
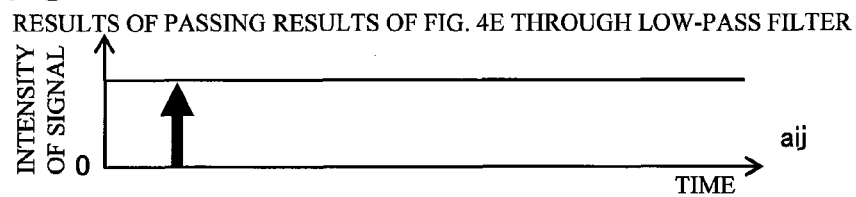

FIG. 9 A
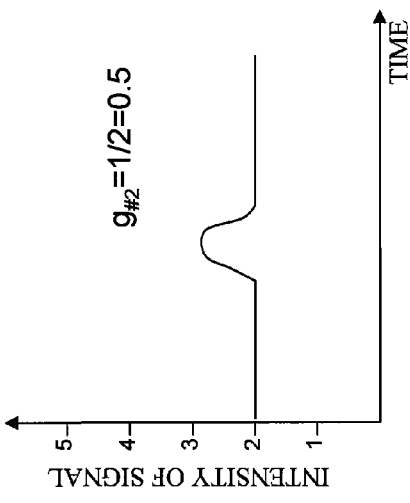
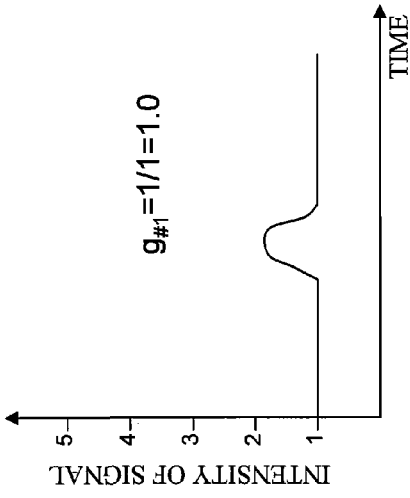
FIG. 9 B
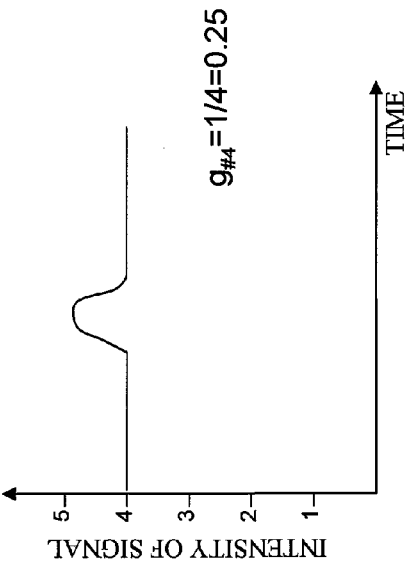
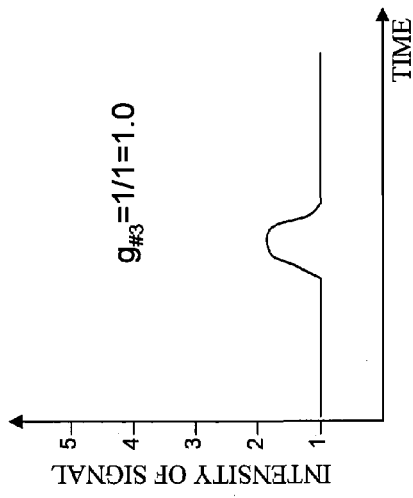

SURFACE INSPECTION METHOD AND SURFACE INSPECTION APPARATUS

BACKGROUND OF THE INVENTION

1. Field of the Invention

The present invention relates to a surface inspection method and a surface inspection apparatus that are intended for detecting micro contaminant particles and defects present on a semiconductor substrate (a semiconductor wafer).

2. Background Art

In production lines of semiconductor substrates (semiconductor wafers), contaminant particles adhering to the substrate surface and defects, such as scratches occurring during processing, are inspected in order to monitor the dust generating condition of the manufacturing equipment. For example, in a semiconductor substrate before the formation of circuit patters, it is necessary to detect micro contaminant particles and defects on the surface to the nearest several tens of nanometers or less. In the above-described inspection of the substrate surface, crystal defects present in a shallow region near the substrate surface and the surface roughness of the substrate surface also become objects to be inspected in addition to the above-described contaminant particles and defects.

As a conventional technique for detecting microdefects on the surface of an objected to be inspected, such as a semiconductor substrate, for examples, as described in U.S. Pat. No. 5,798,829, there has been available an inspection technique that involves forming an illumination spot of a predetermined size by the fixed irradiation of focused laser beams onto the surface of a semiconductor substrate, detecting scattered light from a contaminant particle that is generated in the case of the presence of a contaminant particle adhering to the semiconductor substrate, when the contaminant particle passes through this illumination spot, and inspecting contaminant particles and defects on the whole surface of the semiconductor substrate. In this case, even when a contaminant particle and a defect do not pass through the illumination spot, in the above-described illumination spot, scattered light (hereinafter referred to as background scattered light) is constantly generated due to micro surface roughness (microroughness) on the semiconductor wafer. It is known that in the detection of micro contaminant particles, shot noise deriving from the above-described background scattered light is generally predominant in the noise components of an inspection signal. Because this shot noise is proportional to the square root of the intensity of the light from which the shot noise derives, the noise level in the detection of a micro contaminant particle increases roughly in proportion to the square root of the intensity of background scattered light.

On the other hand, in the case of a micro contaminant particle to which the law of Rayleigh scattering can be applied, when a surface of a semiconductor wafer is irradiated with p-polarization from such a low elevation angle as the Brewster angle to a silicon crystal, it is known that the scattered light from the contaminant particle does not have strong directivity in the direction of azimuthal angle and scattering occurs with almost the same intensity in the directions of all azimuthal angles. In the case of a semiconductor wafer that is polished well, in general, background scattered light deriving from surface roughness does not exhibit extremely strong directivity in the direction of azimuthal angle.

In this case, therefore, from the standpoint of ensuring the S/N ratio of detection signals, it is desirable to detect scattered light diffused in the directions of all azimuthal angles by uniformly focusing the light. In the photodetector of the above-described conventional technique, which collectively receives all of scattered light in the direction of azimuthal angle, a desirable S/N ratio can be obtained.

However, the background scattered light deriving from the surface roughness (microroughness) of a semiconductor surface may sometimes have strong directivity. For example, it is known that in an epitaxial wafer and the like, the background scattered light deriving from the surface roughness depending on a relative relationship between crystal orientation and the direction of illumination may sometimes have strong directivity. In such a case, as described above, a larger noise component is contained in an output signal of a photodetector that performs detection at an azimuthal angle at which the background scattered light deriving from surface roughness is strong. For this reason, it is not advisable that a scattered light signal detected at an azimuthal angle at which the background scattered light deriving from surface roughness is strong and a scattered light signal detected at an azimuthal angle at which the background scattered light deriving from surface roughness is weak are equally treated.

On the other hand, U.S. Pat. No. 7,002,677, which describes a technique for partially cutting off scattered light that travels in a specific direction, claims that it is possible to improve the S/N ratio of scattered light signals from a contaminant particle/defect, which is the object of inspection, by performing control to ensure that a photodetector partially shields the direction of azimuthal angle in which background scattered light is strong and receives scattered light only in the direction of azimuthal angle in which background scattered light is weak.

In the technique described in U.S. Pat. No. 7,002,677, a programmable light selection array is disposed on an optical path between a scattering object and a photodetector, and an azimuthal angle at which background scattered light is strong is partially shielded by controlling this array. In this method, the scattered light in the direction of each azimuthal angle is controlled by "on/off control" in the manner of a selection between the two: "light guiding/light cutting-off" i.e. "using/not using". This applies also to another technique that is similar to the above technique. In this technique, partial cutting-off of scattered light is not performed; instead, among a plurality of photodetectors disposed in a plurality of angular directions, only output signals of a photodetector disposed in the angular direction in which background scattered light is weak are used and output signals of a photodetector disposed in the angular direction in which background scattered light is strong are not used. In these techniques, the scattered light that travels in the angular direction in which output signals from a photodetector are not used, is not received by the photodetector. Therefore, among the light signals included in the scattered light that is not received, the light signal components from a contaminant particle and a defect that are to be detected are discarded without being used. This is valid for a case where "not less than 99.9% of the total quantity of scattered light from a surface of an object to be inspected is background scattered light" as described in U.S. Pat. No. 7,002,677 and does not pose any problem in this case.

However, this poses a problem when the relative ratio of background scattered light to the total quantity of scattered light and the anisotropy of background scattered light in angular directions are not very large as described above. Now think of, for example, a scattered light detection system in which four photodetectors are arranged in four angular directions. If it is assumed that output signals of each photodetector consist of "an aimed signal deriving from the scattered light from a contaminant particle and a defect+a background signal deriving from background scattered light+noise" and that the principal component of the noise is shot noise deriving from background scattered light (this assumption is realistic in many cases), then the noise becomes proportional to the square root of the background signal deriving from background scattered light. For example, it is assumed that the compositions of output signals of the four photodetectors are as shown in "Detector #1" to "Detector #4" of Table 1.

TABLE 1

|  | Aimed signal deriving from the scattered light from a contaminant particle/defect | Background signal deriving from background scattered light | Noise | S/N ratio |
| --- | --- | --- | --- | --- |
| Detector #1 | 1.000 | 1.000 | 1.000 | 1.000 |
| Detector #2 | 1.000 | 2.000 | 1.414 | 0.707 |
| Detector #3 | 1.000 | 1.000 | 1.000 | 1.000 |
| Detector #4 | 1.500 | 4.000 | 2.000 | 0.750 |
| Even addition of #1 to #4 | 4.500 | 8.000 | 2.828 | 1.591 |
| Addition of only #1 and #3 | 2.000 | 2.000 | 1.414 | 1.414 |

At this time, in the two cases: (1) a case where the output signals of the four photodetectors are evenly added and (2) a case where the output signals of photodetectors #1 and #3 are evenly added by not using the output signals of photodetectors #2 and #4 (or by cutting off light so that scattered light does not become incident on photodetectors #2 and #4), the S/N ratio (the ratio of an aimed signal to noise) after addition is as shown in "Even addition of #1 to #4" of Table 1. On the assumption that the noise in each of the photodetectors is statistically independent, synthesized noise is found as the square root of the residual sum of squares of each noise. As is apparent from the results of Table 1, it is apparent that when the relative ratio of background scattered light to the total quantity of scattered light is not very large as described above, there are cases where the method that involves "cutting off light in an angular direction in which background scattered light is strong/not using" is inferior to the method that involves evenly detecting scattered light in all angular directions" in terms of S/N ratio.

The present invention has been made in view of the above circumstances, and provides a surface inspection method and a surface inspection apparatus that are capable of detecting scattered light from a contaminant particle and a defect at a good S/N even when the relative ratio of background scattered light to the total quantity of scattered light and the anisotropy of background scattered light in angular directions is not relatively large in a case where background scattered light deriving from the surface roughness of a semiconductor wafer has directivity in the direction of elevation angles or azimuthal angles and in a case where the directivity of background scattered light changes depending on positions on a wafer to be inspected.

SUMMARY OF THE INVENTION

To solve the above problem, in the surface inspection in accordance with the present invention, light that is scattered, diffracted or reflected on a surface of an object to be inspected or in the vicinity of the surface is detected by use of a plurality of photodetectors in a plurality of directions, and weighted addition processing or weighted averaging processing by a linear combination of a plurality of signals obtained thereby is performed, whereby a contaminant particle and a defect on the surface of the object to be inspected and the like are detected. The size of the contaminant particle and the defect is calculated from results of the weighted addition processing or weighted averaging processing. Incidentally, the weighted addition processing or the weighted averaging processing is performed so that among output signals from the plurality of photodetectors, the contribution rate of an output signal with a high noise level decreases. In order to judge the noise level of output signals from each photodetector, outputs signals from each photodetector are divided into signals for at least two systems: a first divided output signal and a second divided output signal, and signal processing is performed in such a manner that a first signal component corresponding to the intensity of light generated by deriving from the roughness of the surface of the object to be inspected, which belongs to the light scattered, diffracted or reflected from the surface of the object to be inspected or in the vicinity of the surface, is taken out of the first divided output signal, and a second signal component corresponding to the intensity of light generated by deriving from a contaminant particle and a defect on the surface of the object to be inspected or in the vicinity of the surface, which belongs to the light scattered, diffracted or reflected from the surface of the object to be inspected or in the vicinity of the surface, is taken out of the second divided output signal. It is advisable to use a low-pass filter to take out the first signal component, and to use a band-pass filter to take out the second signal component.

That is, the surface inspection method according to the present invention is a surface inspection method for detecting contaminant particles and defects present on a surface of an objected to be inspected or in the interior of the object to be inspected in the vicinity of the surface by irradiating a region of a predetermined size on the surface of the object to be inspected with an irradiation beam, which comprises: a photodetection step of detecting light that derives from the irradiation beam and is scattered, diffracted or reflected on the surface of the object to be inspected or in the vicinity of the surface by use of a plurality of photodetectors in a plurality of directions; and a contaminant particle detection step that involves performing weighted addition processing or weighted averaging processing by linear combination for signals detected by the plurality of photodetectors and detecting a contaminant particle and a defect from results of the weighted addition processing or weighted averaging processing.

The contaminant particle detection step further includes a particle-size calculation step that involves subjecting the second signal component to the weighted addition processing or the weighted averaging processing and calculating the size of the contaminant particle and defect from results of the processing.

In this particle-size calculation step, a calibration curve prepared beforehand by correlating the size of a contaminant particle and a defect to the value of the second signal component generated so as to correspond to the contaminant particle and the defect is provided for each of the plurality of photodetectors, and the size of the contaminant particle and the defect is calculated by applying results, which are obtained by subjecting the second signal component to the weighted addition processing or the weighted averaging processing, to the calibration curve during inspection of the object to be inspected. In the particle-size calculation step, a synthesized calibration curve is prepared by performing weighted addition processing or weighted averaging processing by linear combination from the plurality of calibration curves corresponding to each of the plurality of photodetectors with the aid of the weighting factor, and the size of the contaminant particle and the defect is calculated by applying results, which are obtained by subjecting the second signal component to the weighted addition processing or the weighted averaging processing, to the calibration curve.

The surface inspection method in accordance with the present invention is a surface inspection method for detecting contaminant particles and defects present on a surface of an objected to be inspected or in the interior of the object to be inspected in the vicinity of the surface by irradiating a region of a predetermined size on the surface of the object to be inspected with an irradiation beam, which comprises: a photodetection step that involves detecting light that derives from the irradiation beam and is scattered, diffracted or reflected on the surface of the object to be inspected or in the vicinity of the surface by use of a plurality of photodetectors arranged so as to perform detection in the directions of a plurality of elevation angles or a plurality of azimuthal angles or a combination of a plurality of elevation angles and a plurality of azimuthal angles with respect to the surface of the object to be inspected, and converting the light into electrical signals; a signal processing step that involves dividing output electrical signals from each of the photodetectors into signals for at least two systems, processing a signal for one system through a low-pass filter so as to take out a first signal component corresponding to the intensity of light generated by deriving from roughness of the surface of the object to be inspected, which belongs to the light scattered, diffracted or reflected from the surface of the object to be inspected or in the vicinity of the surface, and processing a signal for the other system through a band-pass filter so as to take out a second signal component corresponding to the intensity of light generated by deriving from a contaminant particle and a defect on the surface of the object to be inspected or in the vicinity of the surface, which belongs to the light scattered, diffracted or reflected from the surface of the object to be inspected or in the vicinity of the surface; a step of amplifying the second signal component at an amplification rate that is inversely proportional to the first signal component; a step of converting the second signal component after amplification into digital data; and a step that involves performing weighted addition processing or weighted averaging processing by linear combination for a plurality of digital data corresponding to signals detected by the plurality of photodetectors and calculating the size of a contaminant particle or a defect from results of the weighted addition processing or weighted averaging processing.

Furthermore, the surface inspection apparatus in accordance with the present invention is a surface inspection apparatus for detecting contaminant particles and defects present on a surface of an object to be inspected or in the interior of the object in the vicinity of the surface by irradiating a region of a predetermined size on the surface of the object to be inspected with an irradiation beam, which comprises: a plurality of photodetectors that detect light that derives from the irradiation beam and is scattered, diffracted or reflected on the surface of the object to be inspected or in the vicinity of the surface at a plurality of azimuthal angles; and contaminant particle detection means that performs weighted addition processing or weighted averaging processing by linear combination for signals detected by the plurality of photodetectors and detects a contaminant particle and a defect from results of the weighted addition processing or weighted averaging processing.

The surface inspection apparatus in accordance with the present invention is a surface inspection apparatus, which comprises: beam irradiation means that irradiates a region of a predetermined size on a surface of an object to be inspected with an beam; an inspection object moving stage that relatively moves the object to be inspected with respect to the beam; a photodetection system that detects light that derives from the beam and is scattered, diffracted or reflected on the surface of the object to be inspected or in the vicinity of the surface, and converts the light into an electrical signal; an A/D converter that converts the electrical signal into digital data; and a particle-size calculation part that calculates the size of a contaminant particle and a defect from the digital data. In this surface inspection apparatus, the photodetection system simultaneously or virtually simultaneously detects an electrical signal or digital data that expresses the intensity of scattered light generated by deriving from microroughness of the surface of the object to be inspected, which belongs to the light scattered, diffracted or reflected on the surface of the object to be inspected or in the vicinity of the surface, and an electrical signal or digital data that represents the intensity of light generated by deriving from a contaminant particle and a defect on the surface of the object to be inspected or in the vicinity of the surface, which belongs to the light scattered, diffracted or reflected on the surface of the object to be inspected or in the vicinity of the surface, in the directions of a plurality of elevation angles or a plurality of azimuthal angles or a combination of a plurality of elevation angles and a plurality of azimuthal angles with respect to the surface of the object to be inspected.

The surface inspection apparatus in accordance with the present invention comprises: beam irradiation means that irradiates a region of a predetermined size on a surface of an object to be inspected with a beam; an inspection object moving stage that relatively moves the object to be inspected with respect to the beam; a photodetection system that detects light that derives from the beam and is scattered, diffracted or reflected on the surface of the object to be inspected or in the vicinity of the surface by use of a plurality of photodetectors arranged so as to perform detection in the directions of a plurality of elevation angles or a plurality of azimuthal angles or a combination of a plurality of elevation angles and a plurality of azimuthal angles with respect to the surface of the object to be inspected, and converts the light into electrical signals; a plurality of A/D converters that convert the electrical signal obtained by the plurality of photodetectors into digital data; and a particle-size calculation part that calculates the size of a contaminant particle or a defect from the digital data. In this surface inspection apparatus, the particle-size calculation part calculates the size of the contaminant particle and the defect by applying the digital data to a calibration curve prepared beforehand by correlating the size of a contaminant particle and a defect to the value of the digital data corresponding to the contaminant particle and the defect for each of the plurality of photodetectors.

Further features of the present invention will become apparent from the preferred embodiments for carrying out the present invention and accompanying drawings, which will be described below.

BRIEF DESCRIPTION OF THE DRAWINGS

FIGS. 2A, 2B and 2C are diagrams showing an example of the configuration of optics 110 used in the surface inspection apparatus in the embodiment; FIG. 2A being a plane view, FIG. 2B being a side view, and FIG. 2C being a detail view;

FIG. 4A to 4G are diagrams showing signal waveforms obtained by the surface inspection apparatus in the embodiment;

FIGS. 9(A) to 9(D) are diagrams to explain Table 2.

DETAILED DESCRIPTION OF THE PREFERRED EMBODIMENTS

As described above, the present invention provides a surface inspection method and a surface inspection apparatus that are capable of detecting scattered light from a contaminant particle and a defect at a good S/N even when the relative ratio of background scattered light to the total quantity of scattered light and the anisotropy of background scattered light in angular directions are not relatively large in a case where background scattered light deriving from the surface roughness of a semiconductor wafer has directivity in the direction of an elevation angle or an azimuthal angle and in a case where the directivity of background scattered light changes depending on positions on a wafer to be inspected. Particularly, when, for example, a surface inspection technique for detecting scattered light by use of a plurality of photodetectors is used in a plurality of directions in which a plurality of elevation angles and a plurality of azimuthal angles are combined, the present invention ensures that a contaminant particle and a defect can be detected at a good S/N ratio by combining output signals from the plurality of photodetectors under optimum conditions.

Embodiments of the present invention will be described in detail below with reference to the accompanying drawings. Incidentally, the present invention is not limited by the embodiments and as a matter or course, modifications to the configuration, additions thereto and substitutions therefore are possible so long as they do not depart from the spirit of the essential scope of the invention.

<Configuration of Surface Inspection Apparatus>

Figure 1:
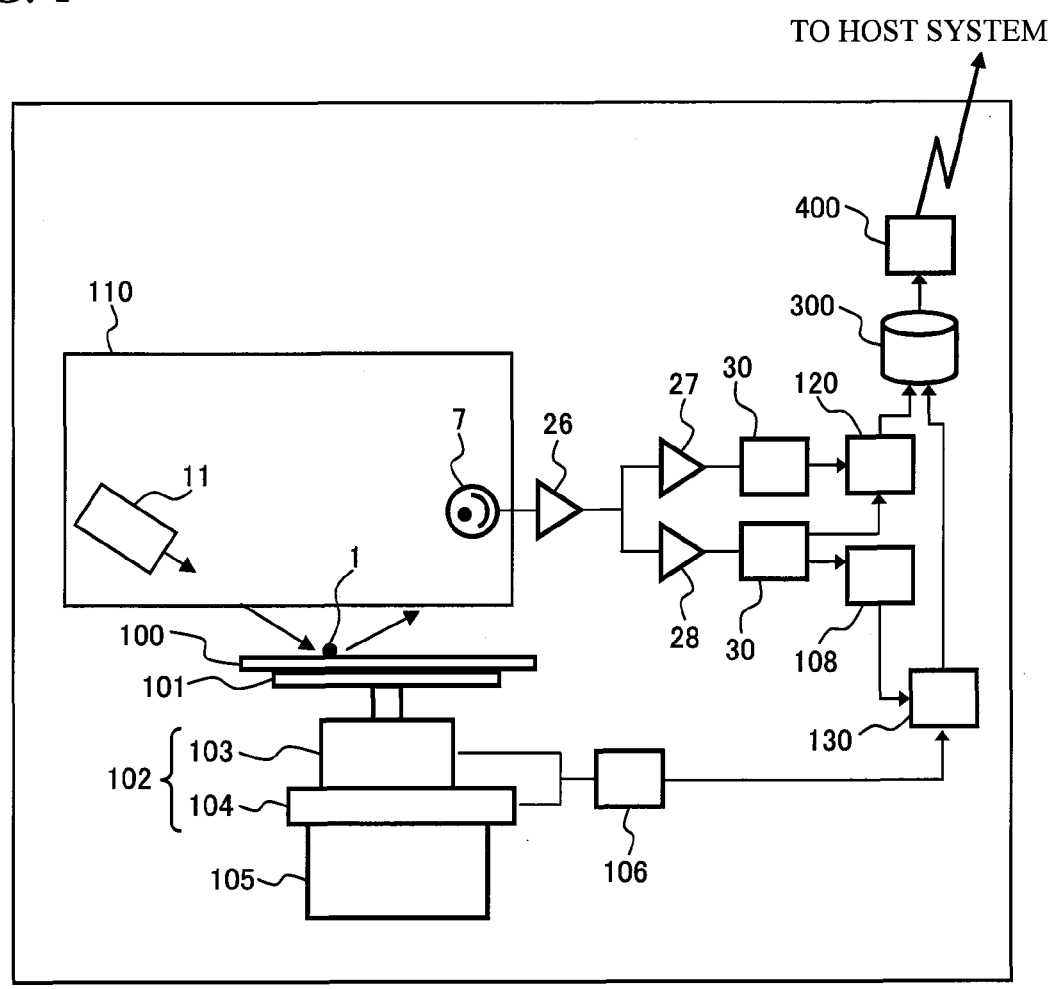
FIG. 1 is a diagram showing the general configuration of a surface inspection apparatus in an embodiment of the present invention.

FIG. 1 is a diagram showing the general configuration of a surface inspection apparatus related to a first embodiment of the present invention. In FIG. 1, a semiconductor wafer 100 that is an object to be inspected is vacuum adsorbed by a chuck 101. This chuck 101 is mounted on an inspection object moving stage 102 constituted by a rotation stage 103 and a translation stage 104, which is mounted on a Z-stage 105. An illumination/detection optics 110 arranged above the semiconductor wafer 100 is provided with a light source 11 and a photodetector 7. In the photodetector 7, for example, the optics shown in FIG. 2, which will be described in detail later, can be used. In the light source 11 of illumination light, it is possible to use a pulse laser that repeatedly performs the pulse oscillation of light having a wavelength in the UV region in terms of time. Light that is irradiated onto the semiconductor wafer 100 and scattered by a contaminant particle 1 present on the semiconductor wafer 100 is detected by the photodetector 7.

The light detected by the photodetector 7 is amplified by a preamplifier 26, and amplified signals are supplied to a low-pass filter 27 and a band-pass filter 28 and divided into signals for two systems. Outputs from each of the systems are converted into digital signals by an A/D converter 30. Incidentally, the system from the photodetector 7 to the A/D converter 30 is shown in FIG. 1 only for one photodetector.

The particle size of the contaminant particle 1 is calculated by a particle-size calculation portion 120, and calculation results are retained in an inspection results retaining part 300. Whether a contaminant particle/defect is present on the semiconductor wafer 100 is detected by a contaminant particle/defect judgment part 108, and information on the presence and nonpresence is supplied to a contaminant particle/defect coordinate inspection part 130. When a contaminant particle/defect has been detected by the coordinate information (values of polar coordinate system γ and θ) obtained by an inspection coordinate inspection part 106, the contaminant particle/defect coordinate inspection part 130 detects the coordinate position and retains the coordinate values in the inspection results retaining part 300. The information retained in the inspection results retaining part 300 (the size of a contaminant particle/defect and the coordinate values thereof) is supplied to an inspection results communication part 400 and supplied to an unillustrated host system via a network and the like.

<Configuration of Illumination/Detection Optics 110>

FIGS. 2A, 2B and 2C are diagrams showing an example of a concrete configuration of the illumination/detection optics 110. In FIGS. 2A, 2B and 2C, an irradiation beam 21 from a light source 11 becomes incident on an irradiation lens 18, and forms an illumination spot 3 of a predetermined size. The illumination light is, for example, p-polarization, and becomes incident on a surface of the semiconductor wafer 100 in an oblique manner substantially at the Brewster angle to a crystal Si. For this reason, the illumination spot 3 has a roughly elliptic shape. The interior of a profile line where illuminance decreases to 1/square of e of the center part of the illumination spot (e is the base of a natural logarithm) is defined here as an illumination spot. The width of a major axis of this illumination spot is denoted by d1 and the width of a minor axis thereof is denoted by d2.

Figure 3:
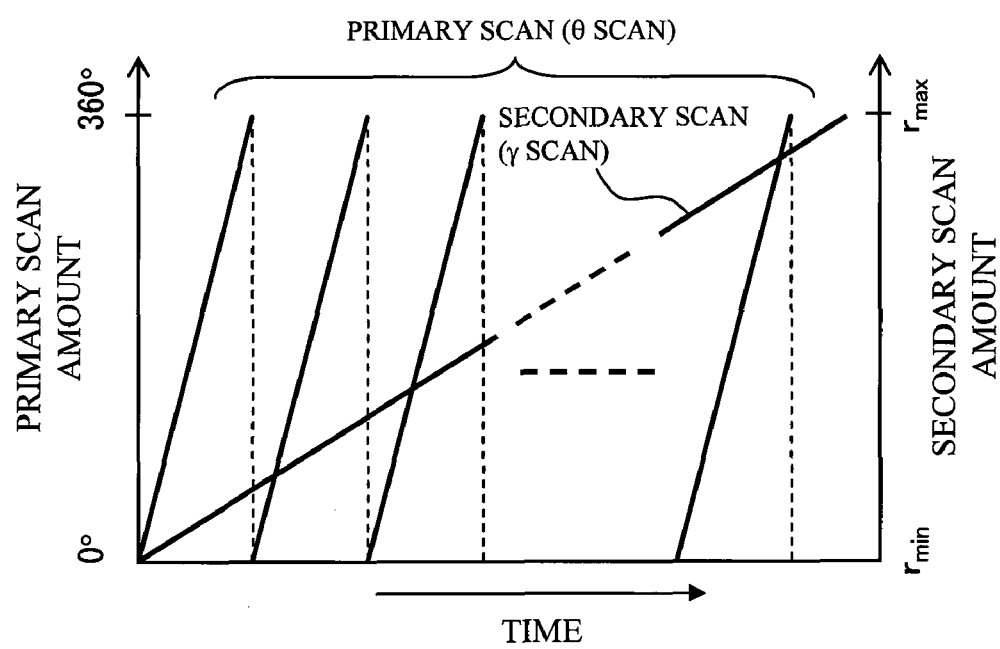
FIG. 3 is a diagram showing a spiral scan driving method of an inspection object moving stage.

The inspection object moving stage 102 changes a rotational movement θ, which provides a primary scan, and a translation movement γ, which provides a secondary scan, with time by combining the two as shown in FIG. 3, and thereby causes the illumination spot 3 to relatively perform spiral scan on the substantially whole surface of the semiconductor wafer 100. While the rotation stage 103 performs one rotation, the secondary scan moves by Δγ. If Δγ>d1, the illumination light is not illuminated onto the semiconductor wafer 100 in the spiral scan and a gap region that is not inspected is produced. Therefore, usually, the relationship is set at Δγ<d1. In this embodiment, the scan by the illumination spot 3 is performed from the inner circumference of the semiconductor wafer 100 to the outer circumference thereof. However, the direction may be reversed. In this embodiment, in the substantially whole region from inner circumference of the semiconductor wafer 100 to the outer circumference thereof, the rotation stage 103 is driven at a substantially constant angular velocity and the translation stage 104 is driven at a substantially constant linear velocity. In order to detect the primary scan coordinate position θ and the secondary scan coordinate position γ during a scan, the inspection object moving stage 102 is provided with the inspection coordinate inspection part 106. In this embodiment, an optical-scan rotary encoder is used in the detection of the primary scan coordinate position θ and an optical-scan linear encoder is used in the detection of the secondary scan coordinate position γ. However, sensors based on other principles may also be used so long as they can detect angles or positions on a straight line at high accuracy.

The scattered/diffracted/reflected light detection system in this embodiment, which is constituted by a plurality of photodetectors 7, is constituted by a first elevation angle detection system 70 and a second elevation angle detection system 80. The first elevation angle detection system 70 has a first elevation angle of approximately 25 degrees so as to be able to efficiently trap the scattered light of a micro contaminant particle to which the law of Rayleigh scattering can be applied, and includes six condenser elements 71 that detect scattered/diffracted/reflected light from six azimuthal angles spaced from each other by approximately 60 degrees each and different from each other with respect to the first scan rotational axis of the inspection object moving stage 102. The second elevation angle detection system 80 has a second elevation angle of approximately 60 degrees, which is larger than the first elevation angle, and includes four condenser elements 81 that detect scattered/diffracted/reflected light from four azimuthal angles spaced from each other by approximately 90 degrees each and different from each other with respect to the first scan rotational axis of the inspection object moving stage 102. Each of the ten condenser elements in all is constituted by a lens, for example. The mechanical arrangement of each of the condenser elements (lenses), particularly that of each of the condenser elements of the first elevation angle detection system 70 may interfere with the optical paths of the irradiation beam 21 and specularly reflected light thereof. Therefore, in this embodiment, each of these condenser elements is arranged so as to avoid the optical paths of the irradiation beam 21 and specularly reflected light thereof.

In this configuration, the contaminant particle 1 passes through the illumination spot 3, and output signals corresponding to the intensity of the scattered/diffracted/reflected light are obtained from the plurality of photodetectors 7. In this embodiment, photomultiplier tubes are used as the photodetectors 7. However, photodetectors based on other principles may also be used so long as they can detect the scattered light from a contaminant particle with high sensitivity.

<Operation of Particle-size Calculation and Detection of Contaminant Particles/Defects>

As shown in FIG. 4, after output signals from each of the photodetectors 7 (see FIG. 4D) are amplified by the preamplifier 26, with a DC signal component contained therein substantially maintained (see FIG. 4E), the output signals are divided into those for two systems. The signal with an amplified output from the photodetector 7 (see FIG. 4E) passes through the low-pass filter 27 and becomes a first divided output signal (see FIG. 4G). The cut-off frequency of this low-pass filter 27 removes a pulse-like component of the signal shown in FIG. 4E, which is generated by the passing of a contaminant particle 1 through the illumination spot 3, and causes virtually only a DC component to pass. As a result, the first signal component obtained as an output of the low-pass filter 27 (see FIG. 4G) largely becomes a signal corresponding to the intensity of light generated by deriving from a microroughness of the surface of the object to be inspected, which belongs to the light scattered/diffracted/reflected on the surface of the object to be inspected or in the vicinity of the surface.

On the other hand, the signal with an amplified output from the photodetector 7 (see FIG. 4E) passes through the band-pass filter 28 and becomes a second divided output signal (see FIG. 4F). The cut-off frequency of this band-pass filter 28 removes a DC component of the signal shown in FIG. 4E, and causes virtually only a pulse-like component, which is generated by the passing of a contaminant particle 1 through the illumination spot 3, to pass. As a result, the second signal component obtained as an output of the band-pass filter 28 (see (f) of FIG. 4) largely becomes a signal corresponding to the intensity of light generated by deriving from a contaminant particle and a defect on the surface of the object to be inspected or in the vicinity of the surface, which belongs to the light scattered/diffracted/reflected on the surface of the object to be inspected or in the vicinity of the surface.

As described above, in the scattered/diffracted/reflected light detection system 110 of this embodiment, combinations of the first signal component and second signal component deriving from output signals of each of the six photodetectors 7 included in the first elevation angle detection system 70 are obtained in six sets, and combinations of the first signal component and second signal component deriving from output signals of each of the four photodetectors 7 included in the second elevation angle detection system 80 are obtained in four sets. These first and second signal components are each sampled by the individual A/D converters 30 and converted into digital data as described above.

Next, the particle-size calculation part 120 calculates the size of a contaminant particle and a defect by using a total of six pieces of digital data $b1j$ ($j=1, 2, 3, 4, 5, 6$) in the first elevation angle system 70 and a total of four pieces of digital data $b2j$ ($j=1, 2, 3, 4$) in the second elevation angle system 80, which are obtained by converting the second signal component. Incidentally, it is known that in the case of detection of a micro contaminant particle, shot noise deriving from the above-described background scattered light is generally predominant in the noise components of an inspection signal. Because shot noise is proportional to the square root of the intensity of light on which the shot noise is based, the noise level occurring in the inspection of a micro contaminant particle increases in proportion to the intensity of background scattered light (noise level $\propto \sqrt{(\text{background scattered light})}$). If the occurring by deriving from the surface roughness of the semiconductor wafer 100 has strong directivity with respect to the directions of azimuthal angles, a large noise component is contained in an output signal of a photodetector that performs detection at an azimuthal angle at which the background scattered light is strong. For this reason, obviously, it is not advisable that an output signal of the photodetector detected at an azimuthal angle at which the background scattered light deriving from surface roughness is strong and an output signal of the photodetector detected at an azimuthal angle at which the background scattered light deriving from surface roughness is weak are equally treated.

Therefore, the particle-size calculation part 120 in this embodiment of the present invention performs weighted addition processing for the digital data $bij$ obtained by converting the second signal component deriving from each of the above-described six and four photodetectors 7 by Equations (1) to (3) below, and obtains a synthesized signal S1 in the first elevation angle detection system 70 and a synthesized signal S2 in the second elevation angle detection system 80.

$$S1 = g11 \times b11 + g12 \times b12 + g13 \times b13 + g14 \times b14 + g15 \times b15 + gp16 \times b16 \quad (1)$$

$$S2 = g21 \times b21 + g22 \times b22 + g23 \times b23 + g24 \times b24 \quad (2)$$

Each of the weighting factors $gij$ is obtained by multiplying the inverse number of digital data $aij$, which is obtained by converting the first signal component deriving from each of the above-described photodetectors 7 by a predetermined proportionality constant K, whereby the quantity of noise is taken into consideration (it is ensured that the larger the noise, the smaller the contribution rate). That is, the following equation holds:

$$gij = K \times 1/aij \qquad (3)$$

In this manner, the weighting factor gij, i.e., the contribution rate of the second signal component obtained from each of the photodetectors 7 to the synthesized signals S1 and S2 decreases as the signal component of the corresponding first signal component increases. Therefore, in the case of a photodetector whose S/N ratio deteriorates because of the occurrence of strong background scattered light due to the directivity of background scattered light as described above, the contribution rate to synthesized signals decreases automatically and it becomes possible to maintain the S/N ratio of synthesized signals at a good level. For this reason, it becomes possible to maintain the S/N ratio of synthesized signals at a good level even when the relative ratio of background scattered light to the total quantity of scattered light and the anisotropy of background scattered light in angular directions are not relatively large in a case where the directivity of background scattered light is strong or in a case where the directivity of background scattered light changes depending on positions on a wafer to be inspected. Examples are shown by real values. When examples of numerical values assumed in Table 1 above are applied to the four photodetectors belonging to the second elevation angle detection system of this embodiment, the results are as given in "weighted addition of #1 to #4" of Table 2.

azimuthal angle in which background scattered light is strong is shielded/not used", and it is evident that a good S/N ratio is obtained even in the case where "the relative ratio of background scattered light to the total quantity of scattered light and the anisotropy of background scattered light in angular directions are large".

The particle-size calculation part 120 converts the synthesized signals S1 and S2 into the size of a contaminant particle and a defect that are detected. However, each of the weighing factors gij changes each time the intensity of the first signal component deriving from each of the photodetectors 7 changes. Therefore, even in the case of the same contaminant particle, the synthesized signals S1 and S2 take different values each time if the intensity and directivity of background scattered light in a position on the semiconductor wafer 100 on which the contaminant particle is present differ. Therefore, no sense is made by the method by which "before the start of inspection, a calibration curve for synthesized signals in which the size of a contaminant particle/defect and the values of the synthesized signals S1 and S2 for the contaminant particle are correlated to each other is prepared beforehand and the size of the contaminant particle and the defect is calculated by applying the values of the synthesized signals S1 and S2 that are obtained every moment during the inspection to the calibration curve for synthesized signals".

In the present invention, therefore, the synthesized signals S1 and S2 are converted into the size of a detected contaminant particle and a defect according to the following steps.

Step 1: Before the start of inspection, an operator prepares calibration wafers to which known standard contaminant par-

TABLE 2

| | Aimed signal deriving from the scattered light from a contaminant particle/defect | Background signal deriving from background scattered light | Weighting factor | Noise | S/N ratio |
|---|---|---|---|---|---|
| Detector #1 | 1.000 | 1.000 | 1.000 | 1.000 | 1.000 |
| Detector #2 | 1.000 | 2.000 | 0.500 | 1.414 | 0.707 |
| Detector #3 | 1.000 | 1.000 | 1.000 | 1.000 | 1.000 |
| Detector #4 | 1.500 | 4.000 | 0.250 | 2.000 | 0.750 |
| Weighted addition of #1 to #4 | 2.875 | 4.000 | — | 1.658 | 1.734 |

In Table 2, because the noise of detectors #1 to #4 is found as the square root of a background signal, the values shown in Table 2 are obtained. As shown in FIG. 9, the weighting factor g#n is found from the inverse number of a background signal from the above equation (Equation 3). The weighting factor g#n for detectors #1 to #4 is respectively as follows: g#n=1.0, g#n=0.5, g#n=1.0, and g#n=0.25. Referring to Table 2, it is apparent that the S/N ratio obtained in a synthesized signal of this embodiment is better than in the method "by which scattered light is evenly detected in the directions of all azimuthal angles" and the method by which "the direction in which background scattered light is strong is shielded/not used", as described above. As a matter of course, in the case where "the relative ratio of background scattered light to the total quantity of scattered light and the anisotropy of background scattered light in angular directions are large", the above-described corresponding weighting factor automatically approaches 0. Therefore, the effect of this method approaches that of the method by which "the direction of an ticles having a plurality of sizes (polystyrene latex (PSL) spheres are desirable) are caused to adhere.

Step 2: The operator sets the inspection conditions of the surface inspection apparatus in this embodiment (the operation conditions of the apparatus for standard contaminant particles, which include, for example, the intensity of an irradiation laser and the size of a laser spot) to adapt to the inspection conditions of inspection performed for an actual wafer that is an object to be inspected.

Step 3: The operator causes inspection of a calibration wafer to be started.

Step 4: For each of the ten photodetectors 7 in all, the surface inspection apparatus of this embodiment records the relationship between the size of each of the detected standard contaminant particles and values of digital data obtained by converting the second signal component generated so as to correspond to the standard contaminant particles.

Step 5: From the relationship between the size of each of the detected standard contaminant particles and values of digital data obtained by converting the second signal component generated so as to correspond to the standard contaminant particles for each of the ten photodetectors 7 in all, the surface inspection apparatus of this embodiment generates and retains a calibration curve for each of the photodetectors 7, i.e., ten calibration curves wij (the first elevation angle inspection system: i=1, j=1, 2, 3, 4, 5, 6; the second elevation angle inspection system: i=2, j=1, 2, 3, 4). wij is a function in the form of, for example, the equation (4) and the value of wij represents the size of a contaminant particle and defect. (Iij: intensity of the second signal component, pij and qij: calibration curve factor).

$$wij(Iij)=pij \times Iij+qij \qquad (4)$$

The preparatory work for calibration curves before inspection are completed with the above steps. Subsequently, wafer inspection is actually performed.

Step 6: The operator causes the inspection of an actual wafer that is an object to be inspected to be started.

Step 7: The surface inspection apparatus of this embodiment generates synthesized signals S1 and S2 by using Equations (1) to (3) for each contaminant particle and each defect that have been detected.

Step 8: The surface inspection apparatus of this embodiment generates a synthesized calibration curve W1 and a synthesized calibration curve W2 from the ten calibration curves wij retained for each of the photodetectors 7 in accordance with Equations (5) and (6).

$$W1=g11 \times w11+g12 \times w12+g13 \times w13+g14 \times w14+g15 \times w15+g16 \times w16 \qquad (5)$$

$$W2=g21 \times w21+g22 \times w22+g23 \times w23+g24 \times w24 \qquad (2)$$

Step 9: The surface inspection apparatus of this embodiment finds the size D1 of a contaminant particle/defect by applying the synthesized signal S1 to the synthesized calibration curve W1 and the size D2 of a contaminant particle/defect by applying the synthesized signal S2 to the synthesized calibration curve W2.

Step 10: In the surface inspection apparatus of this embodiment, D1 is adopted as the size of an inspected contaminant particle/defect when the synthesized signal S1 is larger than the synthesized signal S2, and D2 is adopted in the reverse case.

Figure 5:
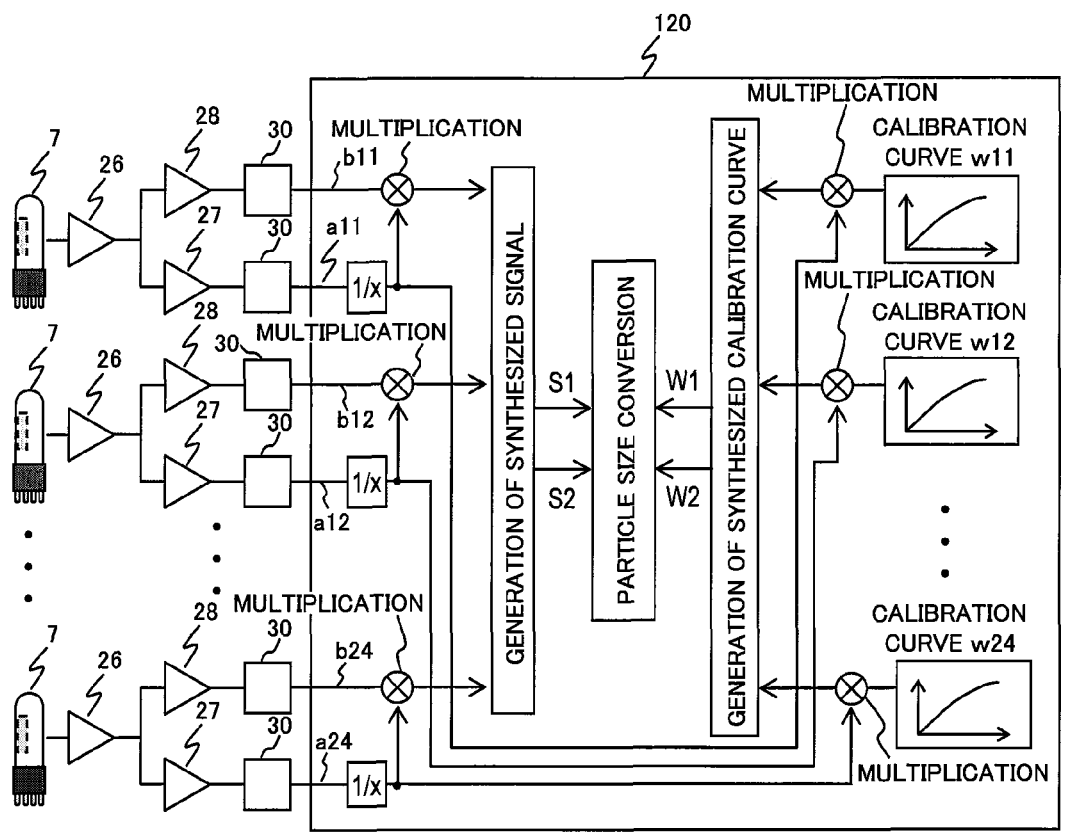
FIG. 5 is a block diagram showing the configuration of the construction of a signal processing part in the surface inspection apparatus of the embodiment.

FIG. 5 is a block diagram showing the configuration of the signal processing part that generates the synthesized signals S1 and S2 and the synthesized calibration curves W1 and W2. In this way, the surface inspection apparatus of this embodiment generates the synthesized calibration curves W1 and W2 obtained by synthesizing the calibration curve for each of the photodetectors by using the same weighting factor as used in the calculation of the synthesized signals S1 and S2. Therefore, the relationship between the synthesized signals S1 and S2 and the synthesized calibration curves W1 and W2 is constantly kept correct, and even when each of the weighting factors gij changes due to a change in the intensity of the first signal component deriving from each of the photodetectors 7, it is possible to correctly perform the conversion of the size of a contaminant particle and a defect. Incidentally, although in this embodiment, photodetectors belonging to the same elevation angle detection system among the plurality of photodetectors are regarded as the object of weighted addition, it is also possible to perform weighted addition for photodetectors including those belonging to different elevation angle detection systems.

When the size of one inspected contaminant particle/defect has been found, the inspection results retaining part 300 stores and retains the value of this size, the above-described weighting factor gij used at this time, each digital data aij and bij, and the position coordinate of the contaminant particle/defect on the semiconductor wafer 100 obtained from the contaminant particle/defect coordinate detection part 130. And when the inspection of the semiconductor wafer 100 has been finished, the inspection results communication part 400 transmits, via a communication network, these pieces of information stored and retained in the inspection results retaining part 300 to a host system that controls the inspection results of a plurality of inspection apparatus. As a result of this, the host system can reproduce the size calculation process for each detected contaminant particle and defect, and can verify whether there has been no abnormality in the size calculation process.

<Modifications>

In the above-described embodiment, a pulse laser that repeatedly performs the pulse oscillation of light having a wavelength in the UV region in terms of time is used in the light source 11 of illumination light. However, the same effect is obtained by using a laser having a wavelength in the visible region and a continuous-wave laser in place of this laser.

Also, in the above-described embodiment, each condenser element of the scattered/diffracted/reflected light detection system comprises a lens. However, concave mirrors may also be used. In the case where a concave mirror is used in a condenser element, as with the foregoing, it is of course possible to adopt an arrangement in which each optical axis of the concave mirror is disposed so as to avoid the optical paths of the illumination beam 21 and the specularly reflected light thereof. However, optical interference may be avoided by providing a through hole, through which these light beams pass, in each interfering mirror surface.

Figure 6:
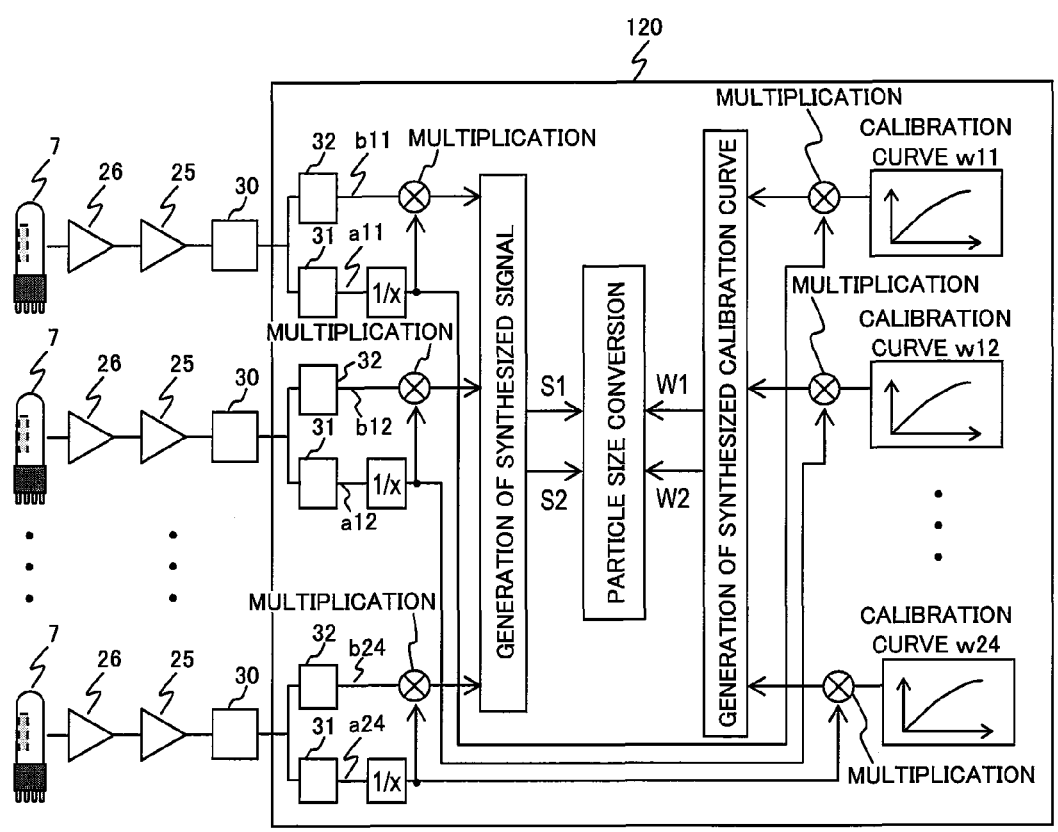
FIG. 6 is a block diagram showing the configuration of the signal processing part in a modification to the present invention.
Figure 7:
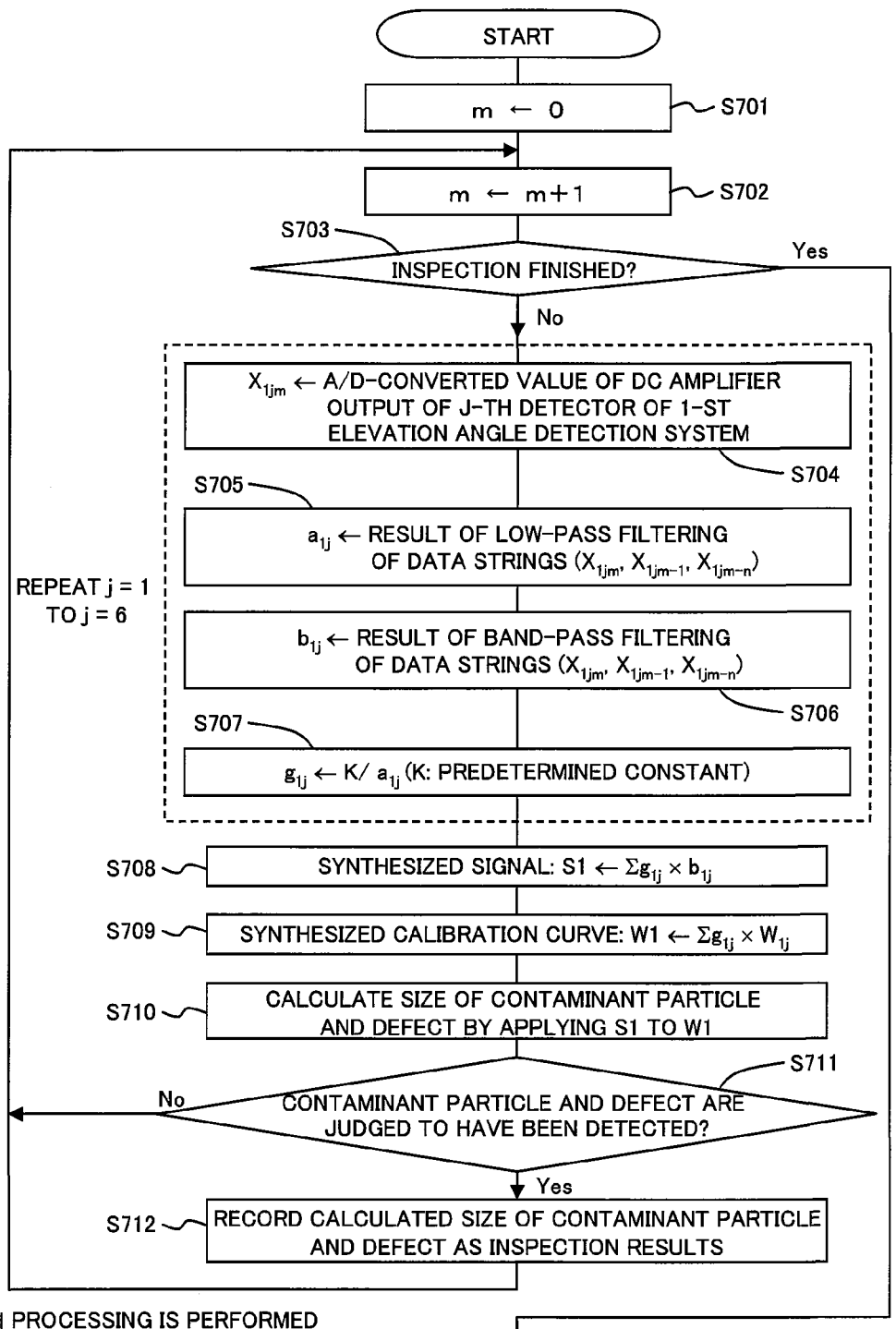
FIG. 7 is a flowchart showing the actions of the signal processing part of FIG. 6.

Furthermore, in the above-described embodiment, a low-pass filter and a band-pass filter are used in the analog circuit before A/D conversion in order to separate the first signal component that corresponds to the intensity of light generated by deriving from mainly the microroughness of the surface of the object to be inspected, which belongs to the light scattered, diffracted or reflected from the surface of the object to be inspected or in the vicinity of the surface, and the second signal component corresponding to the intensity of light generated by deriving from mainly a contaminant particle and a defect on the surface of the object to be inspected or in the vicinity of the surface, which belongs to the light scattered, diffracted or reflected from the surface of the object to be inspected or in the vicinity of the surface. However, in place of this, as shown in FIG. 6, an output signal from each of the photodetectors 7 is amplified, with a DC component contained therein substantially maintained, the amplified output signal is thereafter A/D converted by the A/D converter 30, and low-pass filtering (31) and band-pass filtering (32) are performed in digital signal processing, whereby the first signal component and the second signal component are separated. The same effect is obtained also in this case. FIG. 7 is a flowchart showing processing actions of this modification. A detailed description of this embodiment is omitted because it differs from the above-described embodiment only in the order of A/D conversion. Incidentally, in FIG. 7, the reference character m denotes a variable for expressing the irradiation position of an irradiation beam.

Figure 8:
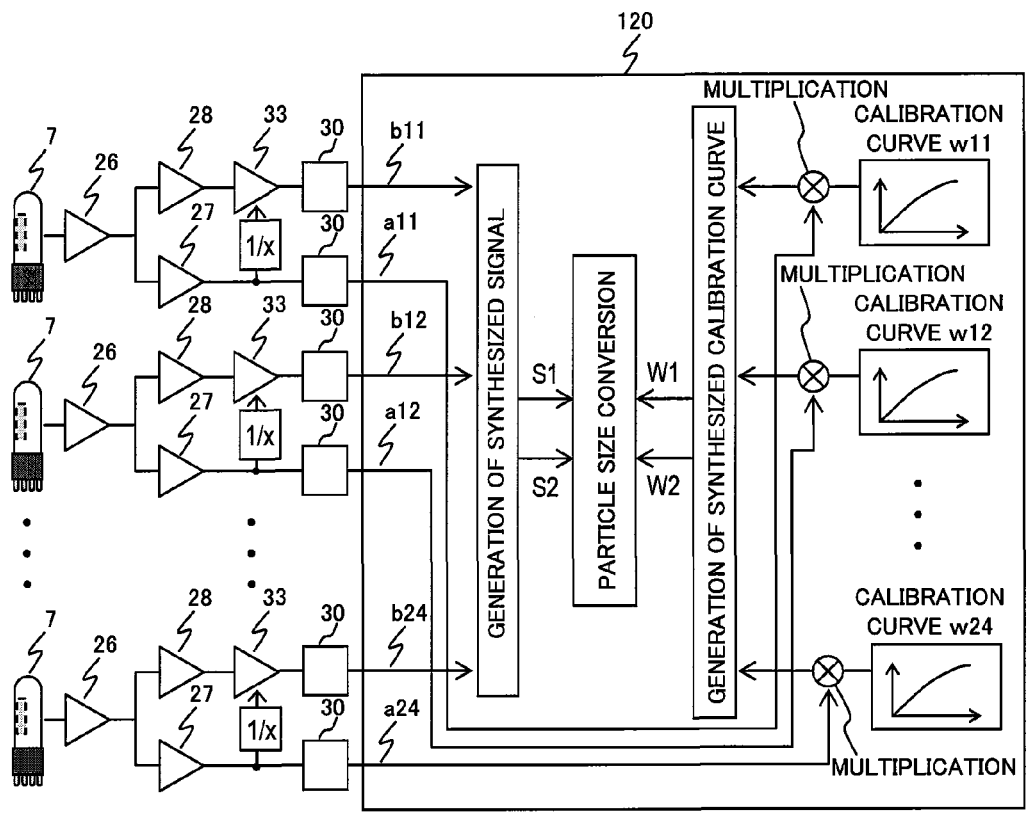
FIG. 8 is a block diagram showing the configuration of a signal processing part in another modification.

Furthermore, as another modification, as shown in FIG. 8, it is also possible to adopt a method that involves separating the first signal component and the second signal component by using a low-pass filter and a band-pass filter in the analog circuit before A/D conversion and thereafter amplifying (33)

the second signal component at an amplification rate that is substantially inversely proportional to the first signal component.

<Summary>

The surface inspection method and surface inspection apparatus in accordance with the present invention can also be described as below.

1. In the present invention, a surface inspection method for detecting the size and position of a contaminant particle and a defect present on a surface of an object to be inspected or in the interior of the object to be inspected in the vicinity of the surface comprises an illumination beam that illuminates a region of a predetermined size on the surface of the object to be inspected, an inspection object moving stage that relatively moves the object to be inspected with respect to the illumination beam, scattering/diffraction/reflection light detection means that detects light that derives from the illumination beam and is scattered/diffracted/reflected on the surface of the object to be inspected or in the vicinity of the surface by use of a plurality of photodetectors arranged so as to perform detection in directions of a plurality of elevation angles or a plurality of azimuthal angles or a combination of a plurality of elevation angles and a plurality of azimuthal angles with respect to the surface of the object to be inspected, and converts the light into electrical signals, a plurality of A/D conversion means that converts the electrical signals obtained from the plurality of photodetectors into digital data, and particle-size calculation means that calculates the size of a contamination particle and a defect from the digital data. In this surface inspection method, the particle-size calculation means includes a function of subjecting a plurality of digital data deriving from the plurality of photodetectors to weighted addition processing or weighted averaging processing by linear combination, and the size of a contaminant particle and a defect is calculated from results of the weighted addition processing or weighted averaging processing. This surface inspection method can be applied to a case where, for example, the noise level is predetermined or the noise level can be a fixed value by a simulation.

2. In the surface inspection method described in item 1 above, the weighted addition processing or the weighted averaging processing is performed so that among detection signals from the plurality of photodetectors, the contribution rate of an output signal with a high noise level decreases.

3. In the surface inspection method described in item 1 or 2 above, the scattering/diffraction/reflection light detection means divides an output signal from each of the photodetectors into signals for at least two systems: a first divided output signal and a second divided output signal, performs signal processing so as to take out, from the first divided output signal, a first signal component corresponding to the intensity of light generated by deriving from mainly the roughness of the surface of the object to be inspected, which belongs to the light scattered, diffracted or reflected from the surface of the object to be inspected or in the vicinity of the surface, and performs signal processing so as to take out, from the second divided output signal, a second signal component corresponding to the intensity of light generated by deriving from mainly a contaminant particle and a defect on the surface of the object to be inspected or in the vicinity of the surface, which belongs to the light scattered, diffracted or reflected from the surface of the object to be inspected or in the vicinity of the surface, the A/D conversion means individually converts the first and second signal components into digital data, the particle-size calculation means determines a weighting factor for the weighted addition processing or the weighted averaging processing by using the digital data obtained by converting the first signal component deriving from each of the photodetectors, and subjects the digital data obtained by converting the second signal component deriving from each of the photodetectors to weighted addition processing or weighted averaging processing. Because this surface inspection method can cope with a case where the weighting factor changes every moment, it is possible to perform appropriate inspection of contaminant particles and defects.

4. In the surface inspection method in item 3 above, means of performing signal processing to take out the first signal component is a low-pass filter, and means of performing signal processing to take out the second signal component is a band-pass filter.

5. In the surface inspection method in item 1 or 2 above, the particle-size calculation means includes signal processing for taking out, by use of the digital data deriving from the output signal of each of the photodetectors, a first signal component corresponding to the intensity of light generated by deriving from mainly the microroughness of the surface of the object to be inspected, which belongs to the light scattered, diffracted or reflected from the surface of the object to be inspected or in the vicinity of the surface, and signal processing for taking out, by use of the digital data deriving from the output signal of each of the photodetectors, a second signal component corresponding to the intensity of light generated by deriving from mainly a contaminant particle and a defect on the surface of the object to be inspected or in the vicinity of the surface, which belongs to the light scattered, diffracted or reflected from the surface of the object to be inspected or in the vicinity of the surface, determines a weighting factor for the weighted addition processing or the weighted averaging processing by using the first signal component, and subjects the second signal component to weighted addition processing or weighted averaging processing.

6. In the surface inspection method described in item 5 above, the scattering/diffraction/reflection light detection means amplifies an output signal from each of the photodetectors, with a DC component contained therein substantially maintained. The signal processing for taking out the first signal component by the particle-size calculation means is low-pass filtering, and the signal processing for taking out the second signal component is band-pass filtering.

7. In the surface inspection method described in any one of items 3 to 6 above, the determination of the weighting factor is performed in such a manner that the larger the first signal component, the ratio at which the second signal component deriving from the photodetector contributes to the weighted addition processing or the weighted averaging processing will be reduced in proportion.

8. In the surface inspection method described in any one of items 3 to 6 above, the determination of the weighting factor is performed in such a manner that that the larger the first signal component, the more the weighting factor of the corresponding second signal component will be reduced.

9. In the surface inspection method described in item 8 above, the weighting factor is determined in proportion to an inverse number of the first signal component.

10. In the surface inspection method described in any one of items 1 to 9 above, the particle-size calculation means has a calibration curve prepared beforehand by correlating the size of a contaminant particle and a defect to the value of the digital data obtained by converting the second signal component generated so as to correspond to the contaminant particle and the defect for each of the plurality of photodetectors, and calculates the size of the contaminant particle and the defect by applying results, which are obtained by subjecting digital data obtained by converting the second signal component deriving from each of the photodetectors to the weighted addition processing or the weighted averaging processing, to the calibration curve during inspection of the object to be inspected.

11. In the surface inspection method described in items 10 above, the particle-size calculation means prepares a synthesized calibration curve by performing weighted addition processing or weighted averaging processing by linear combination from the plurality of calibration curves corresponding to each of the plurality of photodetectors with the aid of the weighting factor, and calculates the size of the contaminant particle and the defect by applying results, which are obtained by subjecting digital data obtained by converting the second signal component deriving from each of the photodetectors to the weighted addition processing or the weighted averaging processing, to the calibration curve.

12. In the present invention, a surface inspection method for detecting the size and position of a contaminant particle and a defect present on a surface of an object to be inspected or in the interior of the object to be detected in the vicinity of the surface comprises an illumination beam that illuminates a region of a predetermined size on the surface of the object to be inspected, an inspection object moving stage that relatively moves the object to be inspected with respect to the illumination beam, scattering/diffraction/reflection light detection means that detects light that derives from the illumination beam and is scattered/diffracted/reflected on the surface of the object to be inspected or in the vicinity of the surface by use of a plurality of photodetectors arranged so as to perform detection in the directions of a plurality of elevation angles or a plurality of azimuthal angles or a combination of a plurality of elevation angles and a plurality of azimuthal angles with respect to the surface of the object to be inspected, and converts the light into electrical signals, a plurality of A/D conversion means that convert the electrical signals obtained from the plurality of photodetectors into digital data, and particle-size calculation means that calculates the size of a contamination particle and a defect from the digital data. In this surface inspection method, the scattering/diffraction/reflection light detection means divides an output signal from each of the photodetectors into signals for at least two systems: a first divided output signal and a second divided output signal, performs processing through a low-pass filter so as to take out, from the first divided output signal, a first signal component corresponding to the intensity of light generated by deriving from mainly the roughness of the surface of the object to be inspected, which belongs to the light scattered, diffracted or reflected from the surface of the object to be inspected or in the vicinity of the surface, and performs processing through a band-pass filter so as to take out, from the second divided output signal, a second signal component corresponding to the intensity of light generated by deriving from mainly a contaminant particle and a defect on the surface of the object to be inspected or in the vicinity of the surface, which belongs to the light scattered, diffracted or reflected from the surface of the object to be inspected or in the vicinity of the surface. After that, the scattering/diffraction/reflection light detection means amplifies the second signal component at an amplification rate that is substantially inversely proportional to the first signal component, the A/D conversion means converts the second signal component after amplification into digital data and the particle-size calculation means subjects the plurality of digital data deriving from the plurality of photodetectors to addition processing or averaging processing.

13. In the present invention, a surface inspection apparatus for detecting the size and position of a contaminant particle and a defect present on a surface of an object to be inspected or in the interior of the object to be inspected in the vicinity of the surface comprises an illumination beam that illuminates a region of a predetermined size on the surface of the object to be inspected, an inspection object moving stage that relatively moves the object to be inspected with respect to the illumination beam, a scattered/diffracted/reflected light detection system that detects light that derives from the illumination beam and is scattered/diffracted/reflected on the surface of the object to be inspected or in the vicinity of the surface by use of a plurality of photodetectors arranged so as to perform detection in the directions of a plurality of elevation angles or a plurality of azimuthal angles or a combination of a plurality of elevation angles and a plurality of azimuthal angles with respect to the surface of the object to be inspected, and converts the light into electrical signals, a plurality of A/D converters that convert the electrical signals obtained from the plurality of photodetectors into digital data, and a particle-size calculation part that calculates the size of a contamination particle and a defect from the digital data. In this surface inspection apparatus, the particle-size calculation part includes a function of subjecting a plurality of digital data deriving from the plurality of photodetectors to weighted addition processing or weighted averaging processing by linear combination, and calculates the size of a contaminant particle and a defect from results of the weighted addition processing or the weighted averaging processing.

14. In the surface inspection apparatus described in item 13 above, the inspection object moving stage is such that a principal scan comprises rotational movements and a secondary scan comprises translation movements.

15. In the surface inspection apparatus described in item 13 or 14 above, the scattered/diffracted/reflected light detection system divides an output signal from each of the photodetectors into signals for at least two systems: a first divided output signal and a second divided output signal, performs signal processing so as to take out, from the first divided output signal, a first signal component corresponding to the intensity of light generated by deriving from mainly the roughness of the surface of the object to be inspected, which belongs to the light scattered, diffracted or reflected from the surface of the object to be inspected or in the vicinity of the surface, and performs signal processing so as to take out, from the second divided output signal, a second signal component corresponding to the intensity of light generated by deriving from mainly a contaminant particle and a defect on the surface of the object to be inspected or in the vicinity of the surface, which belongs to the light scattered, diffracted or reflected from the surface of the object to be inspected or in the vicinity of the surface, the A/D converter individually converts the first and second signal components into digital data, the particle-size calculation part determines a weighting factor for the weighted addition processing or the weighted averaging processing by using the digital data obtained by converting the first signal component deriving from each of the photodetectors, and subjects the digital data obtained by converting the second signal component deriving from each of the photodetectors to weighted addition processing or weighted averaging processing.

16. In the surface inspection apparatus described in item 15 above, means of performing signal processing to take out the first signal component is a low-pass filter and means of performing signal processing to take out the second signal component is a band-pass filter.

17. In the surface inspection apparatus described in item 14 above, the particle-size calculation part includes signal processing for taking out, by use of the digital data deriving from the output signal of each of the photodetectors, a first signal component corresponding to the intensity of light generated by deriving from mainly the microroughness of the surface of the object to be inspected, which belongs to the light scattered, diffracted or reflected from the surface of the object to be inspected or in the vicinity of the surface, and signal processing for taking out, by use of the digital data deriving from the output signal of each of the photodetectors, a second signal component corresponding to the intensity of light generated by deriving from mainly a contaminant particle or a defect on the surface of the object to be inspected or in the vicinity of the surface, which belongs to the light scattered, diffracted or reflected from the surface of the object to be inspected or in the vicinity of the surface, determines a weighting factor for the weighted addition processing or the weighted averaging processing by using the first signal component, and subjects the second signal component to weighted addition processing or weighted averaging processing.

18. In the surface inspection apparatus described in item 17 above, the scattered/diffracted/reflected light detection system amplifies an output signal from each of the photodetectors, with a DC component contained therein substantially maintained, the signal processing for taking out the first signal component in the particle-size calculation part is low-pass filtering, and the signal processing for taking out the second signal component is band-pass filtering.

19. In the surface inspection apparatus described in any of items 15 to 18 above, the weighting factor is determined in proportion to an inverse number of the first signal component.

20. In the surface inspection apparatus described in any of items 14 to 19 above, the particle-size determination part is provided with a calibration curve prepared beforehand by correlating the size of a contaminant particle and a defect to the value of the digital data obtained by converting the second signal component generated so as to correspond to the contaminant particle and the defect for each of the plurality of photodetectors, and calculates the size of the contaminant particle and the defect by applying results, which are obtained by subjecting the digital data obtained by converting the second signal component deriving from each of the photodetectors to the weighted addition processing or the weighted averaging processing, to the calibration curve during inspection of the object to be inspected.

21. In the surface inspection apparatus described in item 20 above, the particle-size calculation part prepares a synthesized calibration curve by performing weighted addition processing or weighted averaging processing by linear combination from the plurality of calibration curves corresponding to each of the plurality of photodetectors with the aid of the weighting factor, and calculates the size of the contaminant particle and the defect by applying results, which are obtained by subjecting the digital data obtained by subjecting the second signal component deriving from each of the photodetectors to the weighted addition processing or the weighted averaging processing, to the calibration curve.

22. The surface inspection apparatus described in item 21 above further comprises an inspection results retaining part that stores and retains the size of each detected contaminant particle and defect calculated by the particle-size calculation part, digital data corresponding to the first and second signal components deriving from each of the photodetectors during the size calculation, the weighting factor used in the size calculation, and position coordinates of the contaminant particle and the defect, and an inspection results communication part that transmits, to a host computer system, inspection results stored and retained in the inspection results retaining part after finish of an inspection of an object to be inspected. As described above, because the weighting factor changes every moment, it is possible to ensure traceability by transmitting the retained weighting factor to the host computer system.

23. In the present invention, a surface inspection apparatus for detecting the size and position of a contaminant particle and a defect present on a surface of an object to be inspected and in the interior of the object to be inspected in the vicinity of the surface comprises an illumination beam that illuminates a region of a predetermined size on a surface of an object to be inspected, an inspection object moving stage that relatively moves the object to be inspected with respect to the illumination beam, a scattered/diffracted/reflected light detection system that detects light that derives from the illumination beam and is scattered, diffracted or reflected on the surface of the object to be inspected or in the vicinity of the surface, and converts the light into an electrical signal, an A/D converter that converts the electrical signal into digital data, and a particle-size calculation part that calculates the size of a contaminant particle and a defect from the digital data. In this surface inspection apparatus, the scattered/diffracted/reflected light detection system simultaneously or virtually simultaneously detects an electrical signal or digital data that represents the intensity of scattered light generated by deriving from mainly microroughness of the surface of the object to be inspected, which belongs to the light scattered, diffracted or reflected from the surface of the object to be inspected or in the vicinity of the surface, and an electrical signal or digital data that represents the intensity of light generated by deriving from mainly a contaminant particle and a defect on the surface of the object to be inspected or in the vicinity of the surface, which belongs to the light scattered, diffracted or reflected from the surface of the object to be inspected or in the vicinity of the surface, in the directions of a plurality of elevation angles or a plurality of azimuthal angles or a combination of a plurality of elevation angles and a plurality of azimuthal angles with respect to the surface of the object to be inspected.

24. In the present invention, a surface inspection apparatus for detecting the size and position of a contaminant particle and a defect on a surface of an object to be inspected or in the interior of the object to be inspected in the vicinity of the surface comprises an illumination beam that illuminates a region of a predetermined size on a surface of an object to be inspected, an inspection object moving stage that relatively moves the object to be inspected with respect to the illumination beam, a scattered/diffracted/reflected light detection system that detects light that derives from the irradiation beam and is scattered, diffracted or reflected on the surface of the object to be inspected or in the vicinity of the surface by use of a plurality of photodetectors arranged so as to perform detection in the directions of a plurality of elevation angles or a plurality of azimuthal angles or a combination of a plurality of elevation angles and a plurality of azimuthal angles with respect to the surface of the object to be inspected, and converts the light into electrical signals, a plurality of A/D converters that convert the electrical signal into digital data, and a particle-size calculation part that calculates the size of a contaminant particle and a defect from the digital data. In this surface inspection apparatus, the particle-size calculation part calculates the size of the contaminant particle and the defect by applying the digital data to a calibration curve prepared beforehand by correlating the size of a contaminant particle and a defect to the value of the digital data corresponding to the contaminant particle and the defect for each of the plurality of photodetectors.

In the surface inspection method or surface inspection apparatus described above, scattered light from various directions is detected and contaminant particles and defects are detected by detection signals of the scattered light by subjecting the detection signals to weighted processing. Therefore, even when the relative ratio of background scattered light to the total quantity of scattered light and the anisotropy of background scattered light in angular directions are not relatively large in a case where background scattered light deriving from the surface roughness of a semiconductor wafer has directivity in the direction of an elevation angle or an azimuthal angle and in a case where the directivity of background scattered light changes depending on positions on a wafer to be inspected, it is possible to detect scattered light from a contaminant particle and a defect at a good S/N by taking the directivity into consideration. Accordingly, it is possible to detect the presence of a contaminant particle and a defect with higher accuracy. Furthermore, it is possible not only to detect the presence of a contaminant particle and a defect, but also to determine the size of the contaminant particle/defect.

Because the presence of a contaminant particle/defect can be detected and the size of the contaminant particle/defect can be determined, it is possible to find at which step among a plurality of steps of the semiconductor manufacturing process many contaminant particles/defects occur. Accordingly, it is possible to improve the yield of the semiconductor manufacturing equipment by improving the identified step.

According to the present invention, even when the directivity of the scattered light deriving from a contaminant particle and a defect and of the scattered light deriving from the surface roughness of a substrate varies, it is possible to inspect the surface of a substrate in a stable manner.

What is claimed is:

1. A surface inspection method for detecting contaminant particles and defects present on a surface of an object to be inspected or in the interior of the object to be inspected in the vicinity of the surface by irradiating a region of a predetermined size on the surface of the object to be inspected with an irradiation beam, comprising:

a photodetection step of detecting light that derives from the irradiation beam and is scattered, diffracted or reflected on the surface of the object to be inspected or in the vicinity of the surface by use of a plurality of photodetectors in a plurality of directions; and a contaminant particle detection step that involves performing weighted addition processing or weighted averaging processing by linear combination for signals detected by the plurality of photodetectors and detecting a contaminant particle and a defect from results of the weighted addition processing or weighted averaging processing;

wherein the weighted addition processing or the weighted averaging processing in the contaminant particle detection step is performed so that among output signals from the plurality of photodetectors, the contribution rate of an output signal with a high noise level decreases;

a signal processing step that involves dividing a plurality of detection signals detected by the plurality of photodetectors into signals for two systems each, and taking out a first signal component generated by deriving from roughness of the surface of the object to be inspected, which belongs to the light scattered, diffracted or reflected from the surface of the object to be inspected or in the vicinity of the surface, and a second signal component generated by deriving from a contaminant particle or a defect on the surface of the object to be inspected or in the vicinity of the surface, which belongs to the light scattered, diffracted or reflected from the surface of the object to be inspected or in the vicinity of the surface, wherein in the contaminant particle detection step, a weighting factor for the weighted addition processing or the weighted averaging processing is determined by using the first signal component and the weighted addition processing or the weighted averaging processing of the second signal component is performed.

2. The surface inspection method according to claim 1, wherein the contaminant particle detection step further comprises a particle-size calculation step that involves subjecting the second signal component to the weighted addition processing or the weighted averaging processing and calculating the size of the contaminant particle and defect from results of the processing.

3. The surface inspection method according to claim 1, wherein in the signal processing step, the first signal component is taken out by a low-pass filter and the second signal component is taken out by a band-pass filter.

4. The surface inspection method according to claim 1, wherein in the contaminant particle detection step, the determination of the weighting factor is performed in such a manner that the larger the first signal component, the ratio at which the corresponding second signal component contributes to the weighted addition processing or the weighted averaging processing will be reduced.

5. The surface inspection method according to claim 1, wherein in the contaminant particle detection step, the determination of the weighting factor is performed in such a manner that the larger the first signal component, the more the weighting factor of the corresponding second signal component will be reduced.

6. The surface inspection method according to claim 5, wherein in the contaminant particle detection step, the weighting factor is determined in proportion to an inverse number of the first signal component.

7. The surface inspection method according to claim 2, wherein in the particle-size calculation step, a calibration curve prepared beforehand by correlating the size of a contaminant particle and a defect to the value of the second signal component generated so as to correspond to the contaminant particle and the defect is provided for each of the plurality of photodetectors, and the size of the contaminant particle and the defect is calculated by applying results, which are obtained by subjecting the second signal component to the weighted addition processing or the weighted averaging processing, to the calibration curve during inspection of the object to be inspected.

8. The surface inspection method according to claim 7, wherein in the particle-size calculation step, a synthesized calibration curve is prepared by performing weighted addition processing or weighted averaging processing by linear combination from the plurality of calibration curves corresponding to each of the plurality of photodetectors with the aid of the weighting factor, and the size of the contaminant particle and the defect is calculated by applying results, which are obtained by subjecting the second signal component to the weighted addition processing or the weighted averaging processing, to the calibration curve.

9. A surface inspection method for detecting contaminant particles and defects present on a surface of an object to be inspected or in the interior of the object to be inspected in the vicinity of the surface by irradiating a region of a predetermined size on the surface of the object to be inspected with an irradiation beam, comprising:
   a photodetection step that involves detecting light that derives from the irradiation beam and is scattered, diffracted or reflected on the surface of the object to be inspected or in the vicinity of the surface by use of a plurality of photodetectors arranged so as to perform detection in the directions of a plurality of elevation angles or a plurality of azimuthal angles or a combination of a plurality of elevation angles and a plurality of azimuthal angles with respect to the surface of the object to be inspected, and converting the light into electrical signals;
   a signal processing step that involves dividing output electrical signals from each of the photodetectors into signals for at least two systems, processing a signal for one system through a low-pass filter so as to take out a first signal component corresponding to the intensity of light generated by deriving from roughness of the surface of the object to be inspected, which belongs to the light scattered, diffracted or reflected from the surface of the object to be inspected or in the vicinity of the surface, and processing a signal for the other system through a band-pass filter so as to take out a second signal component corresponding to the intensity of light generated by deriving from a contaminant particle and a defect on the surface of the object to be inspected or in the vicinity of the surface, which belongs to the light scattered, diffracted or reflected from the surface of the object to be inspected or in the vicinity of the surface;
   a step of amplifying the second signal component at an amplification rate that is inversely proportional to the first signal component;
   a step of converting the second signal component after amplification into digital data; and
   a particle-size calculation step that involves performing weighted addition processing or weighted averaging processing by linear combination for a plurality of digital data corresponding to signals detected by the plurality of photodetectors and calculating the size of a contaminant particle and a defect from results of the weighted addition processing or weighted averaging processing.

10. A surface inspection apparatus for detecting contaminant particles and defects present on a surface of an object to be inspected or in the interior of the object to be inspected in the vicinity of the surface by irradiating a region of a predetermined size on the surface of the object to be inspected with an irradiation beam, comprising:
   a plurality of photodetectors that detect light that derives from the irradiation beam and is scattered, diffracted or reflected on the surface of the object to be inspected or in the vicinity of the surface at a plurality of azimuthal angles; and
   contaminant particle detection means that performs weighted addition processing or weighted averaging processing by linear combination for signals detected by the plurality of photodetectors and detects a contaminant particle and a defect from results of the weighted addition processing or weighted averaging processing;
   wherein the contaminant particle detection means performs the weighted addition processing or the weighted averaging processing so that among output signals from the plurality of photodetectors, the contribution rate of an output signal with a high noise level decreases;
   signal processing means that divides a plurality of detection signals detected by the plurality of photodetectors into signals for two systems, and takes out a first signal component generated by deriving from roughness of the surface of the object to be inspected, which belongs to the light scattered, diffracted or reflected from the surface of the object to be inspected or in the vicinity of the surface, and a second signal component generated by deriving from a contaminant particle or a defect on the surface of the object to be inspected or in the vicinity of the surface, which belongs to the light scattered, diffracted or reflected from the surface of the object to be inspected or in the vicinity of the surface,
   wherein the contaminant particle detection means determines a weighting factor for the weighted addition processing or the weighted averaging processing by using the first signal component and performs the weighted addition processing or the weighted averaging processing of the second signal component.

11. The surface inspection apparatus according to claim 10, wherein the contaminant particle detection means further comprises particle-size calculation means that subjects the second signal component to the weighted addition processing or the weighted averaging processing and calculates the size of the contaminant particle and the defect from results of the processing.

12. The surface inspection apparatus according to claim 10, wherein the signal processing means takes out the first signal component by a low-pass filter and takes out the second signal component by a band-pass filter.

13. The surface inspection apparatus according to claim 10, wherein the contaminant particle detection means determines the weighting factor in proportion to an inverse number of the first signal component.

14. The surface inspection apparatus according to claim 11, wherein the particle-size calculation means provides a calibration curve prepared beforehand by correlating the size of a contaminant particle and a defect to the value of the second signal component generated so as to correspond to the contaminant particle and the defect for each of the plurality of photodetectors, and calculates the size of the contaminant particle and the defect by applying results, which are obtained by subjecting the second signal component to the weighted addition processing or the weighted averaging processing, to the calibration curve during inspection of the object to be inspected.

15. The surface inspection apparatus according to claim 14, wherein the particle-size calculation means prepares a synthesized calibration curve by performing weighted addition processing or weighted averaging processing by linear combination from the plurality of calibration curves corresponding to each of the plurality of photodetectors with the aid of the weighting factor, and calculates the size of the contaminant particle and the defect by applying results, which are obtained by subjecting the second signal component to the weighted addition processing or the weighted averaging processing, to the calibration curve.

16. The surface inspection apparatus according to claim 15, further comprising:
an inspection results retaining part that stores and retains the size of each detected contaminant particle and defect calculated by the particle-size calculation part, data corresponding to the first and second signal components deriving from each of the photodetectors during the size calculation, the weighting factor used in the size calculation, and position coordinates of the contaminant particle and defect, and
an inspection results communication part that transmits, to a host computer system, inspection results stored and retained in the inspection results retaining part after finish of an inspection of an object to be inspected.

17. A surface inspection apparatus, comprising:
beam irradiation means that irradiates a region of a predetermined size on a surface of an object to be inspected with a beam;
an inspection object moving stage that relatively moves the object to be inspected with respect to the beam;
a photodetection system configured to detect light derived from the irradiation beam and is scattered, diffracted or reflected on the surface of the object to be inspected or in the vicinity of the surface, and to convert the light into an electrical signal;
an A/D converter that converts the electrical signal into digital data; and
a particle-size calculation part that calculates the size of a contaminant particle and a defect from the digital data,
wherein the photodetection system is arranged to obtain a first electrical signal and a second electrical signal from the electrical signal, and simultaneously or virtually simultaneously to detect the first electrical signal or that expresses the intensity of scattered light generated by deriving from microroughness of the surface of the object to be inspected, which belongs to the light scattered, diffracted or reflected from the surface of the object to be inspected or in the vicinity of the surface, and the second electrical signal that represents the intensity of light generated by deriving from a contaminant particle and a defect on the surface of the object to be inspected or in the vicinity of the surface, which belongs to the light scattered, diffracted or reflected from the surface of the object to be inspected or in the vicinity of the surface, in the directions of a plurality of elevation angles or a plurality of azimuthal angles or a combination of a plurality of elevation angles and a plurality of azimuthal angles with respect to the surface of the object to be inspected.

18. A surface inspection apparatus, comprising:
beam irradiation means that irradiates a region of a predetermined size on a surface of an object to be inspected with a beam;
an inspection object moving stage that relatively moves the object to be inspected with respect to the beam;
a photodetection system that detects light that derives from the beam and is scattered, diffracted or reflected on the surface of the object to be inspected or in the vicinity of the surface by use of a plurality of photodetectors arranged so as to perform detection in the directions of a plurality of elevation angles or a plurality of azimuthal angles or a combination of a plurality of elevation angles and a plurality of azimuthal angles with respect to the surface of the object to be inspected, and converts the light into electrical signals;
a plurality of A/D converters that convert the electrical signal obtained from the plurality of photodetectors into digital data; and
a particle-size calculation part that calculates the size of a contaminant particle and a defect from the digital data,
wherein the particle-size calculation part calculates the size of the contaminant particle and the defect by applying the digital data to a calibration curve prepared beforehand by correlating the size of a contaminant particle and a defect to the value of the digital data corresponding to the contaminant particle and the defect for each of the plurality of photodetectors.

* * * * *